US006365549B2

(12) United States Patent
Sisler

(10) Patent No.: US 6,365,549 B2
(45) Date of Patent: Apr. 2, 2002

(54) METHODS OF BLOCKING AN ETHYLENE RESPONSE IN PLANTS USING CYCLOPROPENE DERIVATIVES

(75) Inventor: Edward C. Sisler, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/789,142

(22) Filed: Feb. 20, 2001

Related U.S. Application Data

(63) Continuation-in-part of application No. 09/448,523, filed on Nov. 23, 1999, now Pat. No. 6,194,350.
(60) Provisional application No. 60/193,202, filed on Mar. 30, 2000.

(51) Int. Cl.$^7$ .......................... A01N 27/00; A01N 29/02
(52) U.S. Cl. ........................................ 504/114; 504/357
(58) Field of Search .................................. 504/114, 357

(56) References Cited

U.S. PATENT DOCUMENTS

| | | | |
|---|---|---|---|
| 3,879,188 A | 4/1975 | Fritz et al. ...................... 71/86 |
| 5,100,462 A | 3/1992 | Sisler et al. ................... 71/121 |
| 5,518,988 A | 5/1996 | Sisler et al. ................. 504/114 |
| 6,194,350 B1 | 2/2001 | Sisler ......................... 504/114 |

FOREIGN PATENT DOCUMENTS

| | | | |
|---|---|---|---|
| EP | 0 030 287 A1 | 6/1981 | ......... C07C/143/78 |
| WO | WO 95/33377 | 12/1995 | ............ A01N/3/00 |

OTHER PUBLICATIONS

Sisler et al., "Control of Ethylene Responses at the Receptor Level", Biology Biotechnology Plant Hormone Ethylene II, [Proc. EU–TMR–Euroconf. Symp.], 45–50 (1999) (Abstract).
International Search Report, PCT/US00/31944, Date of Mailing Jul. 23, 2001.
M.C. Pirrung, *Proposal to the Fred C. Gioeckner Foudation* (1991).
Pirrung et al. "Ethylene Biosynthesis, Aminocyclopropene Carboxylic Acid", J. Chem. Soc., Chem. Commun., (13), 857–859 (1989).
Wheeler et al., "Synthesis of 1–Aminocyclopropene Carboxylic Acid", J. Org. Chem., 52(22) 4875–4877 (1987).
ACS Registry, Registration No. 3569–41–3 (1999).
ACS Registry, Regstration No. 50915–82–7 (1999).
ACS Registry, Registration No. 50915–83–8 (1999).
ACS Registry, Regstration No. 503–05–9 (1999).
ACS Registry, Registration No. 5026–66–4 (1999).
ACS Registry, Registration No. 18325–59–2 (1999).
ACS Registry, Registration No. 18459–83–1 (1999).
ACS Registry, Registration No. 28634–53–9 (1999).
ACS Registry, Registration No. 50915–84–9 (1999).
ACS Registry, Registration No. 79246–40–5 (1999).
ACS Registry, Registration No. 223105–97–3 (1999).
ACS Regsitry, Registration No. 35365–52–7 (1999).
ACS Registry, Registration No. 35365–53–8 (1999).
ACS Registry, Registration No. 1089–40–3 (1999).
ACS Registry, Registration No. 178493–45–3 (1999).
ACS Registry, Registration No. 24471–15–6 (1999).
ACS Registry, Registration No. 141493–84–7 (1999).
ACS Registry, Registration No. 152389–89–4 (1999).
ACS Registry, Regstration No. 24471–16–7 (1999).
ACS Regstry, Regstration No. 152389–90–7 (1999).
ACS Regstry, Regstration No. 3565–59–1 (1999).
ACS Regstry, Regstration No. 183888–59–7 (1999).
ACS Regstry, Registration No. 102179–95–3 (1999).
ACS Regstry, Regstration No. 183888–58–6 (1999).
ACS Regstry, Regstration No. 738–87–4 (1999).
ACS Regstry, Regstration No. 39647–67–1 (1999).
ACS Regstry, Regstration No. 39647–66–0 (1999).
ACS Regsrty, Regstration No. 3220–60–8 (1999).
ACS Regstry, Regstration No. 39647–65–9 (1999).
ACS Regstry, regstration No. 152442–29–0 (1999).
ACS regstry, Regstration No. 13487–77–9 (1999).
ACS Regstry, Regstration No. 183888–62–2 (1999).
ACS Regsrty, Regstration No. 183888–63–3 (1999).
ACS Regstry, Regstration No. 183888–65–5 (1999).
ACS Regstry, Regstration No. 109154–74–7 (1999).
ACS Regstry, Regstration No. 102127–48–0 (1999).

*Primary Examiner*—S. Mark Clardy
(74) *Attorney, Agent, or Firm*—Myers Bigel Sibley & Sajovec, P.A.

(57) ABSTRACT

Methods of applying $C_{5-20}$ cyclopropene derivatives and compositions thereof to block ethylene receptors in plants are disclosed. One such method comprises applying to the plant an effective ethylene response-inhibiting amount of cyclopropene derivatives or compositions thereof. Also disclosed are methods of inhibiting abscission in plants, methods of prolonging the life of cut flowers, methods of inhibiting ripening of picked fruits, and methods of inhibiting ripening of picked vegetables.

30 Claims, No Drawings

METHODS OF BLOCKING AN ETHYLENE RESPONSE IN PLANTS USING CYCLOPROPENE DERIVATIVES

RELATED APPLICATIONS

This application is a continuation-in-part of commonly owned, application Ser. No. 09/448,523 of Edward C. Sisler, filed Nov. 23, 1999, now U.S. Pat. No. 6,194,350 the disclosure of which is incorporated by reference herein in its entirety. This application also claims priority from Edward C. Sisler, U.S. Provisional Application No. 60/193,202, filed Mar. 30, 2000, the disclosure of which is incorporated by reference herein in its entirety.

GOVERNMENT SUPPORT

This invention was made with government support under Grant No. US-2786-96R awarded by the U.S. Department of Agriculture. The government has certain rights in the invention.

FIELD OF THE INVENTION

The present invention generally relates to methods of blocking ethylene responses in plants and plant materials, and particularly relates to methods of inhibiting various ethylene responses including plant maturation and degradation by applying cyclopropene derivatives and compositions thereof to plants.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; others prevent ethylene from binding and thereby counteract its action.

Many compounds that block the action of ethylene do so by binding to the ethylene binding site. Unfortunately, they often diffuse from the binding site over a period of several hours. See E. Sisler and C. Wood, *Plant Growth Reg.* 7, 181–191 (1988). These compounds may be used to counteract ethylene action. A problem with such compounds, however, is that exposure must be continuous if the effect is to last for more than a few hours.

Photoaffinity labeling has been used in biological studies to label binding sites in a permanent manner: usually by generating a carbene or nitrene intermediate. Such intermediates are very reactive and react rapidly and indiscriminately with many things. A compound already bound, however, would react mostly with the binding site. In a preliminary study, it was shown that transcyclooctene was an effective blocking agent for ethylene binding. See E. Sisler et al., *Plant Growth Reg.* 9, 157–164 (1990). Methods of combating the ethylene response in plants with diazocyclopentadiene and derivatives thereof are disclosed in U.S. Pat. No. 5,100,462 to Sisler et al. U.S. Pat. No. 5,518,988 to Sisler et al. describes the use of cyclopropenes having a $C_1$ to $C_4$ alkyl group to block the action of ethylene.

Notwithstanding these efforts, there remains a need in the art for improved plant maturation and degradation regulation.

SUMMARY OF THE INVENTION

Methods of inhibiting an ethylene response in a plant are disclosed herein. According to the present invention, one such method comprises applying to the plant an effective ethylene response-inhibiting amount of a cyclopropene derivative or a composition thereof described further in detail herein. Long-chain cyclopropene derivatives are particularly preferred as described below.

Another aspect of the present invention is a method of blocking ethylene receptors in plants by applying to the plants an effective ethylene receptor-blocking amount of a cyclopropene derivative or a composition thereof.

Also disclosed is a method of inhibiting abscission in a plant, comprising applying to the plant an effective abscission-inhibiting amount of a cyclopropene derivative or a composition thereof.

Also disclosed is a method of prolonging the life of a cut flower, comprising applying to the cut flower an effective life-prolonging amount of a cyclopropene derivative or a composition thereof.

Also disclosed is a method of inhibiting the ripening of a harvested fruit, comprising applying to the harvested fruit an effective inhibiting amount of a cyclopropene derivative or a composition thereof.

Also disclosed is a method of inhibiting the ripening of a harvested vegetable, comprising applying to the harvested vegetable an effective inhibiting amount of a cyclopropene derivative or a composition thereof.

The methods described herein may be carried out in a number of suitable manners, such as by contacting the plant with a cyclopropene derivative or a composition thereof, whether in solid, liquid, or gaseous form, or by introducing the plant, cut flower, picked fruit or picked vegetable into an atmosphere infused with the cyclopropene derivative or a composition thereof. These and other suitable methods of application are discussed in detail below.

Also disclosed is the use of a cyclopropene derivative as described herein for the preparation of an agricultural composition for carrying out any of the methods described above.

DETAILED DESCRIPTION OF THE INVENTION

Cyclopropene derivatives which may be used to carry out the present invention are defined by Formula I:

(I)

wherein:

n is a number from 1 to 4. Preferably n is 1 or 2, and most preferably n is 1.

R is a saturated or unsaturated, linear or branched-chain, unsubstituted or substituted, $C_5$ to $C_{20}$ alkyl, alkenyl, or alkynyl.

The terms "alkyl", "alkenyl", and "alkynyl", as used herein, refer to linear or branched alkyl, alkenyl or alkynyl substituents. The terms should be interpreted broadly and may include compounds in which one or more of the carbons in one or more of the R groups is replaced by a group such as ester groups, nitriles, amines, amine salts, acids, acid salts, esters of acids, hydroxyl groups, halogen groups, and heteroatoms selected from the group consisting of oxygen and nitrogen or where such chains include halogen, amino, alkoxy, carboxy, alkoxycarbonyl, oxycarbonylalkyl, or hydroxy substituents. Thus, the resulting R groups can contain, for example, hydroxyl, ether, ketone, aldehyde, ester, acid, acid salt, amine, amine salt, amide, oxime, nitrile, and halogen groups.

Cyclopropene derivatives which may be used to carry out the present invention may be prepared by various methods known to those skilled in the art. For example, the reaction of a bromo-olefin with dibromocarbene gives a tribromocyclopropane, which can be converted to the cyclopropene with methyllithium or other organolithium compounds as shown. (see Baird, M. S.;

Hussain, H. H.; Nethercott, W; *J. Chem. Soc. Perkin Trans.* 1, 1986, 1845–1854 and Baird, M. S.; Fitton, H. L.; Clegg, W; McCamley, A.; *J. Chem. Soc. Perkin Trans.* 1, 1993, 321–326).

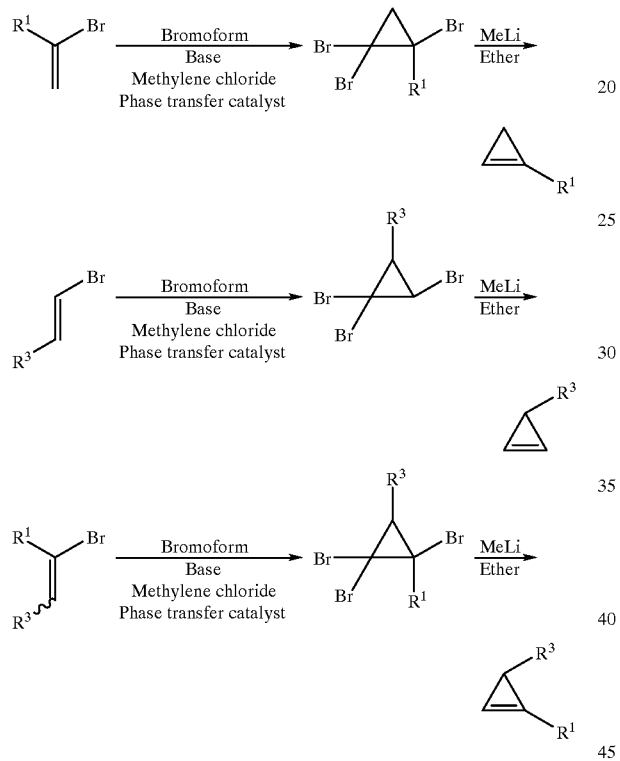

The bromo-olefins can be prepared by standard methods.

Additionally, 3,3-disubstituted cyclopropenes can be prepared using methods described by N. I. Yakushkina and I. G. Bolesov in *Dehydrohalogenation of Monohalogenocyclopropanes as a Method for the Synthesis of Sterically Screened Cyclopropenes*, RUSSIAN J. OF ORGANIC CHEM. 15:853–59 (1979). Furthermore, a 1,1-disubstituted olefin can also react with dibromocarbene to give a dibrominated intermediate. This can be reduced with zinc to the monobrominated cyclopropane. Elimination of the bromide with base gives the cyclopropene (see Binger, P.; *Synthesis* 1974, 190).

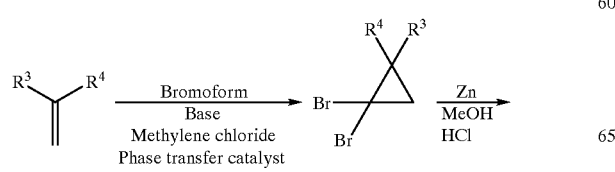

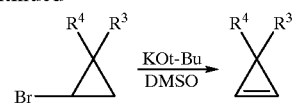

Cyclopropene can be deprotonated with a strong base such as sodium amide in liquid ammonia and alkylated with an alkyl halide or other alkylating agent to give a substituted cyclopropene (reference: Schipperijn, A. J.; Smael, P.; *Recl. Trav. Chim. Pays-Bas,* 1973, 92, 1159). The lithium salt of substituted cyclopropenes, generated from the cyclopropene or by reaction of the tribromocyclopropane with an alkyllithium, can be alkylated to give new cyclopropene derivatives.

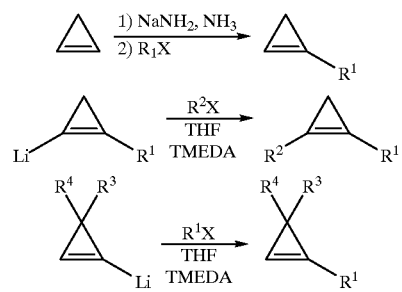

Compounds according to the present invention can also be obtained from a malonate derivative as shown.

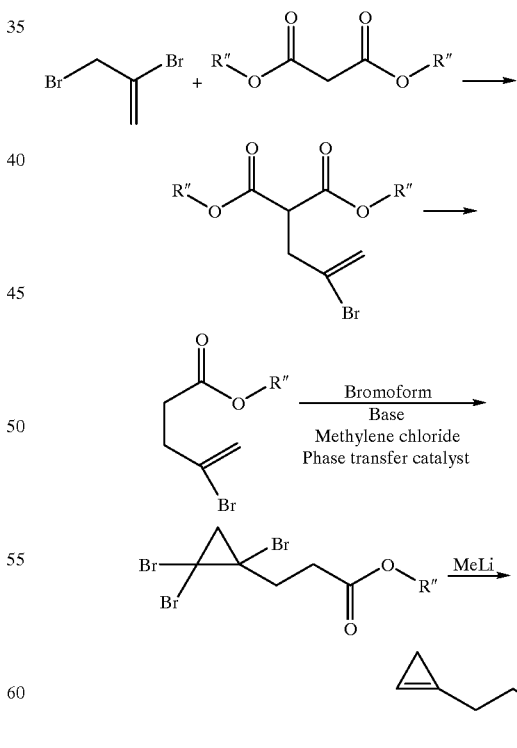

Methyl sterculate was formed by the procedure of Gensler et. al. (Gensler, W. J.; Floyd, M. B.; Yanase, R.; Pober, K. W. *J. Am. Chem. Soc.,* 1970, 92, 2472).

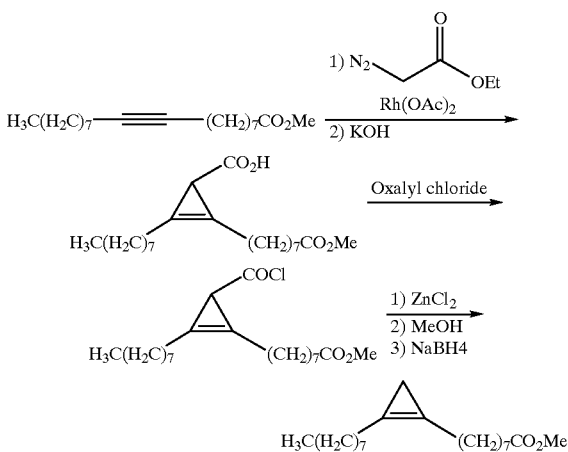

The addition of a diazo compound to an acetylene is another method that can be used for the synthesis of cyclopropenes (Mueller, P.; Cranisher, C; *Helv. Chim. Acta* 1993, 76, 521). Alternatively, the commercially available ethyl diazo acetate can be added to the acetylene to give the compound:

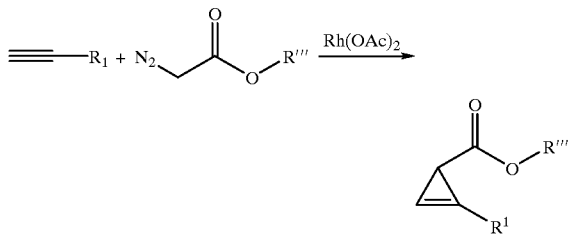

with R''' being ethyl. This compound can be hydrolyzed to the carboxylic acid, and reacted with oxalyl chloride to give the acid chloride. The acid chloride can then be reacted with an alcohol to give the ester. In the foregoing synthesis routes, $R^1$–$R^4$ are as described above for R.

Agricultural compositions comprising the compounds defined by Formula (I) described above are also encompassed by the invention. Preferably the compositions comprise between a lower limit of 0.005, 5, 10, 20 or 30% and an upper limit of 70, 80, 90, 95 or 99% by weight of the active compounds of the present invention. These compositions may optionally include various additives typically found in agricultural compositions including, but not limited to, carriers, adjuvants, wetting agents and the like.

Numerous organic solvents may be used as carriers for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can also be employed as inert carriers for the active compounds.

The active compounds of the present invention may also include adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyceride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids (e.g., Ethofat® 7 and 13, commercially available from Akzo Nobel Chemicals, Inc. of Chicago, Ill.), sodium N-methyl-N-oleyltaurate, Turkey Red oil, sodium dibutylnaphthalene sulfonate, sodium lignin sulfonate (Marasperse® N, commercially available from Ligno Tech USA of Rothschild, Wis.), polyethylene glycol stearate, sodium dodecylbenzene sulfonate, tertiary dodecyl polyethylene glycol thioether, long chain ethylene oxide-propylene oxide condensation products (e.g., Pluronic® 61 (molecular weight 1,000) commercially available from BASF of Mount Olive, N.J.), sorbitan sesquioleate, polyethylene glycol ester of tall oil acids, sodium octyl phenoxyethoxyethyl sulfate, polyoxyethylene (20) sorbitan monolaurate (Tween® 20, commercially available from ICI Americas Inc. of Wilmington, Del.) tris(polyoxyethylene) sorbitan monostearate (Tween® 60, commercially available from ICI Americas Inc. of Wilmington, Del.), and sodium dihexyl sulfosuccinate.

The solid, liquid, and gaseous formulations can be prepared by various conventional procedures. Thus, the active ingredient, in finely divided form if a solid, may be tumbled together with finely divided solid carrier. Alternatively, the active ingredient in liquid form, including mixtures, solutions, dispersions, emulsions and suspensions thereof, may be admixed with the solid carrier in finely divided form. Furthermore, the active ingredient in solid form may be admixed with a liquid carrier to form a mixture, solution, dispersion, emulsion, suspension or the like.

The active compounds of the present invention can be applied to plants by various suitable means. For example, an active compound may be applied alone in gaseous, liquid, or solid form by contacting the compound with the plant to be treated. Additionally the active compound may be converted to the salt form, and then applied to the plants. Alternatively, compositions containing one or more active compounds of the present invention may be formed. The compositions may be applied in gaseous, liquid, or solid form by contacting the composition with the plant to be treated. Such compositions may include an inert carrier. Suitable solid carriers include dusts. Similarly, when in gaseous form, the compound may be dispersed in an inert gaseous carrier to provide a gaseous solution. The active compound may also be suspended in a liquid solution such as an organic solvent or an aqueous solution that may serve as the inert carrier. Solutions containing the active compound may be heterogeneous or homogeneous and may be of various forms including mixtures, dispersions, emulsions, suspensions and the like.

The active compounds and compositions thereof can also be applied as aerosols, e.g., by dispersing them in air using a compressed gas such as dichlorodifluoromethane, trichlorofluoromethane, and other Freons, for example.

The term "plant" is used in a generic sense herein, and includes woody-stemmed plants such as trees and shrubs. Plants to be treated by the methods described herein include whole plants and any portions thereof, such as field crops, potted plants, cut flowers (stems and flowers), and harvested fruits and vegetables.

Plants treated with the compounds and by the methods of the present invention are preferably treated with a non-phytotoxic amount of the active compound.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the shortening of life of ornamentals such as potted plants, cut flowers, shrubbery, seeds, and dormant seedlings, in some plants (e.g., pea) the inhibition of growth, and in other plants (e.g., rice) the stimulation of growth. Additional ethylene responses or ethylene-type responses that may be inhibited by active compounds of the present invention include, but are not limited to, auxin activity, inhibition of terminal growth, control of apical dominance, increase in branching, increase in tillering, changing bio-chemical compositions of plants (such as increasing leaf area relative to stem area), abortion or inhibition of flowering and seed development, lodging effects, stimulation of seed germination and breaking of dormancy, and hormone or epinasty effects.

Methods according to embodiments of the present invention inhibit the ripening and/or senescence of vegetables. As used herein, "vegetable ripening" includes the ripening of the vegetable while still on the vegetable-bearing plant and the ripening of the vegetable after having been harvested from the vegetable-bearing plant. Vegetables which may be treated by the method of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (Daucus), bulbs, such as onions (Allium sp.), herbs, such as basil (*Ocimum basilicum*), oregano (*Origanum vulgare*), dill (*Anethum graveolens*), as well as soybean (*Glycine max*), lima beans (*Phaseolus limensis*), peas (Lathyrus spp.), corn (*Zea mays*), broccoli (*Brassica oleracea italica*), cauliflower (*Brassica oleracea botrytis*), and asparagus (*Asparagus officinalis*).

Methods according to embodiments of the present invention inhibit the ripening of fruits. As used herein, "fruit ripening" includes the ripening of fruit while still on the fruit-bearing plant as well as the ripening of fruit after having been harvested from the fruit-bearing plant. Fruits which may be treated by the method of the present invention to inhibit ripening include tomatoes (*Lycopersicon esculentum*), apples (*Malus domestica*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (Citrus sp.), lemons (*Citrus limonia*), limes (*Citrus aurantifolia*), grapefruit (*Citrus paradisi*), tangerines (*Citrus nobilis deliciosa*), kiwi (*Actinidia chinenus*), melons such as cantaloupe (*C. cantalupensis*) and musk melon (*C. melo*), pineapple (*Aranas comosus*), persimmon (Diospyros sp.), various small fruits including berries such as strawberries (Fragaria), blueberries (Vaccinium sp.) and raspberries (e.g., *Rubus ursinus*), green beans (*Phaseolus vulgaris*), members of the genus Cucumis such as cucumber (*C. sativus*), and avocados (*Persea americana*).

Ornamental plants which may be treated by the method of the present invention to inhibit senescence and/or to prolong flower life and appearance (e.g., delay wilting), include potted ornamentals, and cut flowers. Potted ornamentals and cut flowers which may be treated with the present invention include azalea (Rhododendron spp.), hydrangea (*Macrophylla hydrangea*), hybiscus (*Hibiscus rosasanensis*), snapdragons (Antirrhinum sp.), poinsettia (*Euphorbia pulcherima*), cactus (e.g. *Cactaceae schlumbergera truncata*), begonias (Begonia sp.), roses (Rosa spp.), tulips (Tulipa sp.), daffodils (Narcissus spp.), petunias (*Petunia hybrida*), carnation (*Dianthus caryophyllus*), lily (e.g., Lilium sp.), gladiolus (Gladiolus sp.), alstroemeria (*Alstoemeria brasiliensis*), anemone (e.g., *Anemone blanda*), columbine (Aquilegia sp.), aralia (e.g., *Aralia chinensis*), aster (e.g., *Aster carolinianus*), bougainvillea (Bougainvillea sp), camellia (Camellia sp.), bellflower (Campanula sp.), cockscomb (celosia sp.), falsecypress (Chamaecyparis sp.), chrysanthemum (Chrysanthemum sp.), clematis (Clematis sp.), cyclamen (Cyclamen sp.), freesia (e.g., *Freesia refracta*), and orchids of the family Orchidaceae.

Plants which may be treated by the method of the present invention to inhibit abscission of foliage, flowers and fruit include cotton (Gossypium spp.), apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*ficus benjamina*), as well as dormant seedlings such as various fruit trees including apple, ornamental plants, shrubbery, and tree seedlings. In addition, shrubbery which may be treated according to the present invention to inhibit abscission of foliage include privet (Ligustrum sp.), photinea (Photinia sp.), holly (Ilex sp.), ferns of the family Polypodiaceae, schefflera (Schefflera sp.), aglaonema (Aglaonema sp.), cotoneaster (Cotoneaster sp.), barberry (Berberis sp.), waxmyrtle (Myrica sp.), abelia (Abelia sp.), acacia (Acacia sp.) and bromeliades of the family Bromeliaceae.

Active compounds of the present invention have proven to be unexpectedly potent inhibitors of ethylene action on plants, fruits and vegetables, even when applied at low concentrations. Among other things, compounds of the present invention may result in a longer period of insensitivity to ethylene than compounds found in the prior art. This longer period of insensitivity may occur even when compounds of the present invention are applied at a lower concentration than previous compounds.

The present invention is explained in greater detail in the following non-limiting Examples. In these examples, $\mu l$ means microliters; ml means milliliters; nl means nanoliters; l means liters; cm means centimeters; and temperatures are given in degrees Celsius.

Comparative Example A

Activity of Short-Chain Cyclopropene Derivatives

To obtain the minimum concentration that protected bananas from 333 $\mu l/l$ of ethylene, compounds described in U.S. Pat. No. 5,518,988 to Sisler et al. were applied to bananas according to the methods setforth herein. A known amount of an active compound was injected as a gas into a 3-liter jar containing a banana. The jar was sealed and the banana was removed after 24 hours. At the end of exposure, the banana was treated with 333 pill of ethylene in a 3-liter jar for 12–15 hours. It was then observed for ripening. The minimum concentration is the minimum concentration that protected the banana from 333 $\mu$l/l of ethylene. Ten microliters/liter of ethylene is usually considered to be a saturating amount.

To obtain the time of protection, bananas were exposed to a saturating amount of the compound for 24 hours (this was done as above and at least 10 times the minimum protection amount was used). After exposure, bananas were removed from the jars and each day individual bananas were exposed to 333 pill of ethylene for 12–15 hours. The day the bananas responded to ethylene was recorded as the protection time. The results are shown in Table A.

TABLE A

Minimum Concentration and Time of Insensitivity for 1-Cyclopropenes Described in U.S. Pat. No. 5,518,988 to Sisler et al.

| Compound | Structure | Concentration (nl/l) | Time (days) |
|---|---|---|---|
| cyclopropene (CP) | △ | 0.7 | 12 |
| 1-methylcyclopropene (1-MCP) | △—CH$_3$ | 0.7 | 12 |
| 1-ethylcyclopropene (1-ECP) | △—CH$_2$CH$_3$ | 4 | 12 |
| 1-propylcyclopropene (1-PCP) | △—CH$_2$CH$_2$CH$_3$ | 6 | 12 |
| 1-butylcyclopropene (1-BCP) | △—CH$_2$(CH$_2$)$_2$CH$_3$ | 3 | 12 |

EXAMPLE 1

Compounds of the Present Invention: Minimum Concentration for Protection

To obtain the minimum concentration that protected bananas from 333 $\mu$l/l of ethylene, compounds according to the present invention were applied to bananas according to the method described herein. A known amount of the active compound was placed on filter paper in a 3-liter jar to facilitate evaporation into the vapor state. The compounds were applied in an ethyl ether solution because the amount used was potentially too small to apply unless they were in solution. The amount of ether (about 10 $\mu$l in 3 l) was without effect when applied alone on a banana contained in a 3-liter jar. The jar was sealed and the banana was removed after 4 hours of exposure. At the end of exposure, the banana was treated with 333 $\mu$l/l of ethylene in a 3-liter jar for 12–15 hours. It was then observed for ripening. The minimum concentration is the concentration that protected the bananas from 333 $\mu$l/l of ethylene. Ten microliters/liter of ethylene is usually considered to be a saturating amount. This procedure was repeated for 8-, 24- and 48-hour treatment times to determine the minimum concentration of active compounds of the present invention needed to provide protection from 333 $\mu$l/l of ethylene for a given treatment time. The results are shown in Table 1.

TABLE 1

Treatment Time and Minimum Concentration of 1-Cyclopropenes of the Present Invention on Banana Fruit

| Active Compound | Treatment Time (hours) | Minimum Concentration (nl/l) |
|---|---|---|
| 1-hexylcyclopropene | 4 | 12.0 |
|  | 8 | 0.8 |
|  | 24 | 0.4 |
|  | 48 | 0.3 |
| 1-octylcyclopropene | 4 | 0.8 |
|  | 8 | 0.45 |
|  | 24 | 0.3 |
|  | 48 | 0.25 |

EXAMPLE 2

Compounds of the Present Invention: Time of Protection

To obtain the time of protection, bananas were exposed to a saturating amount of the compound for 24 hours (this was done as described in Example 1 above and at least 10 times the minimum protection amount was used). After exposure, bananas were removed from the jars and each day individual bananas were exposed to 333 $\mu$l/l of ethylene for 12–15 hours. The day the bananas responded to ethylene was recorded as the protection time. The results are shown in Table 2.

TABLE 2

Minimum Concentration and Time of Insensitivity for 1-Cyclopropenes Provided by the Present Invention

| Compound | Structure | Concentration (nl/l) | Time (days) |
|---|---|---|---|
| 1-hexylcyclopropene (1-HCP) | △—CH$_2$(CH$_2$)$_4$CH$_3$ | 0.4 | 20 |
| 1-octylcyclopropene (1-OCP) | △—CH$_2$(CH$_2$)$_6$CH$_3$ | 0.3 | 25 |

EXAMPLES 3 THROUGH 29

In general, all cyclopropenes are stored at −80° C. All reactions were carried out under an atmosphere of nitrogen. Flash chromatography of cyclopropenes was carried out under an atmosphere of nitrogen. All target compounds were 80% or greater purity unless otherwise noted.

EXAMPLE 3

Preparation of N,N'-dibenzyl-N,N,N',N'-tetramethylethylenediammonium Dibromide and N, N'-dibenzyl-N,N,N',N'-tetraethylethylenediammonium Dibromide To a stirred solution of 16.5 g (142 mmol) of N,N,N',N'-tetramethylethylenediamine in 60 g of acetonitrile was added 50.1 g (292 mmol) of benzyl bromide. The mixture self warmed and was allowed to stir for 2.5 hours whereon a heavy precipitate was observed. The slurry was diluted with diethyl ether, filtered, washed with diethyl ether and dried yielding 61.8 g of the desired N,N'-dibenzyl-N,N,N', N'-tetramethylethylenediammonium dibromide, a white solid mp 230–232° C.

In an analogous way, using N,N,N',N'-tetraethylethylenediamine one obtains N,N'-dibenzyl-N,N,N',N'-tetraethylethylenediammonium dibromide, a white solid mp 190–193° C., decomposes.

EXAMPLE 4

Preparation of 1-Hexyl-cyclopropene (Compound 1)

a. 2-Bromo-oct-1-ene

A solution of 9.42 ml (0.0728 mol) of 2,3-dibromopropene in 70 ml diethylether was placed under a nitrogen atmosphere by use of a Firestone valve. While cooling in an ice water bath, a solution of 0.091 mol of pentylmagnesium bromide in 70 ml diethyl ether was added slowly via addition funnel. After stirring for 2 hours while warming to room temperature, there was then added via syringe 50 ml of 1 N hydrochloric acid to the reaction cooling in an ice water bath. The resulting mixture was transferred to a separatory funnel and the phases were separated. The organic layer was dried over $MgSO_4$ and filtered. The solvent was removed from the filtrate in vacuo to yield 15.0 g (85.7% of theory) of 81% pure 2-bromo-oct-1-ene as an oil.

b. 1,1,2-Tribromo-2-hexyl-cyclopropane

To 5.42 g (0.0284 mol) of 2-bromo-oct-1-ene in 7.42 ml (0.0851 mol) of bromoform and 48.8 ml of methylene chloride, were added 1.30 g ( 0.00284 mol) of N,N'-dibenzyl-N,N,N',N'-tetramethylethylenediammonium dibromide and 12.1 ml (0.142 mol) of 45% aqueous potassium hydroxide. The mixture was left at room temperature for 5 days. There was then added hexanes and water. This mixture was gravity filtered through qualitative fluted filter paper. The resulting mixture was transferred to a separatory funnel and the phases were separated. The organic layer was dried over $MgSO_4$ and filtered. The solvent was removed from the filtrate in vacuo to yield 5.25 g (51.0% of theoretical) of 1,1,2-tribromo-2-hexyl-cyclopropane as an oil.

c. 1-Hexyl-cyclopropene

A solution of 1.01 g (0.00278 mol) of 1,1,2-tribromo-2-hexyl-cyclopropane in 4 ml of diethyl ether was placed under a nitrogen atmosphere via use of a Firestone valve. While cooling in an ice water bath, 6.3 ml (0.00835 mol) of 1.4M methyl lithium in diethyl ether was added slowly by syringe. After 15 minutes, 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield 0.300 g (87% of theoretical) of 1-hexyl-cyclopropene pure as an oil.

EXAMPLE 5

Preparation of 3-Octylcyclopropene (Compound 2)

1-Bromo-dec-1-ene was prepared by the method of Millar et al (Millar, J. G.; Underhill, E. W.; *J. Org. Chem.* 1986, 51, 4726). This olefin was converted to 3-octylcyclopropene in a similar manner to the preparation of 70% pure 1-hexylcyclopropene.

EXAMPLE 6

Preparation of 1-(7-Methoxyheptyl)-cyclopropene (Compound 3)

6-Bromohexyl methyl ether was prepared from 1,6-dibromohexane. To 48.8 g (200 mmol) of 1,6-dibromohexane at 60° C. was added 44 g (200 mmol) of a 25% solution of sodium methoxide in methanol. The reaction mixture was held 0.5 hours, then an additional 4 g of sodium methoxide solution was added, and the reaction mixture was held an additional hour. Hexane and water were added, the organic phase was washed with brine and dried with magnesium sulfate, filtered and stripped. Fractional distillation under vacuum gave 93% pure 6-bromohexyl methyl ether. This bromide was converted to the Grignard reagent, which was converted to 1-(7-methoxyheptyl)-cyclopropene in the same manner that pentylmagnesium bromide was converted to 1-hexylcyclopropene.

EXAMPLE 7

Preparation of 1-(Undec-5-ynl)-cyclopropene (Compound 4)

1-Bromodec-4-yne was prepared from 1-chlorodec-4-yne. The 1-chlorodec-4-yne (10.6 g, 61 mmol) and 25 g of lithium bromide were refluxed in 80 ml of THF for 21 hours. The conversion was 74%. Ether was added, the reaction mixture was washed with water (2×) and brine, dried over magnesium sulfate and stripped. The product was dissolved in 70 ml of THF and refluxed for 8 hours with an additional 25 g of lithium bromide. This gave 95% conversion of the chloride to the bromide. The same workup provided 11.36 g of 1-bromodec-4-yne.

The 1-bromodec4-yne was converted to the Grignard reagent in THF. The Grignard reagent was converted to 1-(undec-5-ynl)-cyclopropene in the same manner that pentylmagnesium bromide was converted to 1-hexylcyclopropene.

EXAMPLE 8

Preparation of 1-(7-Hydroxyheptyl)-cyclopropene (Compound 5)

a. 1-(1-Ethoxyethoxy)-6-bromohexane

To a cooled solution of 80 mg of toluenesulfonic acid in 40 ml of ether was fed 20 g (110 mmol) of 6-bromohexanol and 40 ml of ethyl vinyl ether simultaneously by separate additional funnels. The temperature of the reaction mixture was kept at 7° C. or lower during the feeds, which took 1 hour. The reaction mixture was stirred 20 minutes longer, then roughly 1 ml of triethylamine was added. The reaction mixture was washed with water and brine, dried over potassium carbonate, filtered and stripped to give 25.7 g of a pale yellow liquid, which was used without further purification.

b. 9-(1-Ethoxyethoxy)-2-bromonon-1-ene

A slurry of 5.6 g of magnesium turnings (230 mmol) in 100 ml of THF was treated with a small amount of 1,2-dibromoethane. 1-(1-Ethoxyethoxy)-6-bromohexane (38.5 g, 152 mmol) was fed slowly to the reaction mixture, maintaining the temperature at 40–50° C. At the end of the addition the reaction mixture was held 20 minutes, then transferred by cannula to solution of 33.4 9 (167 mmol) of 1,2-dibromoprop-2-ene in 25 ml of THF at 0C. The reaction mixture was stirred at 0° C. for 15 minutes, then stirred at room temperature for 15 minutes, then quenched with water. The reaction mixture was transferred into a separatory funnel. A small amount of 1 N HCl was added, the phases were separated, the ether phase was washed with water and brine, then dried over magnesium sulfate, filtered, and stripped to give 33.63 g of a yellow liquid which was used without further purification.

c. 1,1,2-Tribromo-2-(7-hydroxyheptyl)cyclopropane

A mixture of 9-(1-ethoxyethoxy)-2-bromonon-1-ene (33.63 g, 115 mmol), 4.1 g of N,N'-dibenzyl-N,N,N',N'-tetraethylethylenediammonium dibromide, 42 g of 45% potassium hydroxide (337 mmol), 93 g of bromoform (368 mmol) and 280 g of methylene chloride were rapidly stirred at room temperature for two days. When the reaction stalled, the reaction mixture was transferred to a separatory funnel and washed with water. The methylene chloride phase was transferred to a flask and treated with the same amount of the phase transfer catalyst and 45% potassium hydroxide, then stirred at room temperature for an additional 3 days. The reaction mixture was washed with water, the methylene chloride phase was dried with magnesium sulfate, and then stripped. The product was treated with 320 ml of methanol and 40 ml of 1 N HCl for 1 hour at room temperature. The methanol was stripped, ethyl acetate was added. The organic phase was washed with water and brine, then treated with 200 ml of silica gel. Filtration followed by a strip gave 38 g of black product. This was chromatographed on silica gel to give 19.0 g of 1,1,2-tribromo-2-(7-hydroxyheptyl) cyclopropane as a pale yellow liquid.

d. 1-(7-Hydroxyheptyl)-cyclopropene

A solution of 1.0 g 1,1,2-tribromo-2-(7-hydroxyheptyl) cyclopropane (2.5 mmol) in 25 ml of ether was treated at −78° C. with 7.2 ml of methyllithium (1.4 M, 10 mmol). After 5 minutes, the reaction mixture was warmed to 0° C. and held at this temperature. The reaction was quenched with saturated ammonium chloride. The reaction mixture was washed with water and brine, dried over magnesium sulfate, filtered and stripped to give 240 mg of 1-(7-hydroxyheptyl)-cyclopropene (90% purity).

EXAMPLE 9

Preparation of 1-(7-Acetoxyheptyl)-cyclopropene (Compound 6)

A solution of 2.5 mmol of 1-(7-hydroxyheptyl)-cyclopropene in 5 ml of ether was cooled in an ice bath. Triethylamine (0.44 ml) and 0.21 g (2.7 mmol) of acetyl chloride were added, and the reaction mixture was stirred 1 hour at 5° C. Additional acetyl chloride (0.11 g), ether and triethylamine were added, and the reaction was stirred at 5° C. until GC analysis indicated 95% conversion. The reaction was worked up by adding more ether and washing the organic phase with water, dilute HCl solution (diluted 1M aqueous HCl), potassium carbonate solution (2×), water and brine. The ether phase was dried over magnesium sulfate and stripped. Hexane was added and the reaction was stripped again to give 1-(7-acetoxyheptyl)-cyclopropene.

EXAMPLE 10

Preparation of 7-Cycloprop-1-enyl-heptanoic Acid (Compound 7)

a. 7-(1,1,2-Tribromo-cyclopropyl)-heptanoic acid 1,1,2-Tribromo-2-(7-hydroxyheptyl)cyclopropane (0.90 g, 2.3 mmol) was dissolved in 60 ml of glacial acetic acid. A solution of 1.0 g (10 mmol) of chromium trioxide dissolved in 14 ml of 90% aqueous acetic acid was added and the reaction mixture was stirred at room temperature for 24 hours. Water (300 ml) was added. The solution was extracted with ether. The ether phase was extracted three times with 1N NaOH solution. A little sodium bisulfite was added. The aqueous extracts were acidified with 6N HCl, and extracted with ether twice. The ether extracts were washed with brine, dried over magnesium sulfate and stripped to give 0.56 g 7-(1,1,2-tribromo-cyclopropyl)-heptanoic acid.

b. 7-Cycloprop-1-enyl-heptanoic acid 1,1,2-Tribromo-2-(7-carboxyheptyl)-cyclopropane (1.28 g, 3.1 mmol) was dissolved in 60 ml of ether and cooled to −78° C. Methyllithium (9.0 ml, 12.6 mmol) was added and the reaction was stirred at −78° C. for two hours. The reaction mixture was put in an ice bath for 5 minutes, then recooled to −78° C. until workup. Water was added to the reaction mixture, which was warmed to room temperature. The aqueous phase was separated, and the ether phase was extracted with three times with 1N NaOH solution. The combined aqueous extracts were acidified with aqueous HCl, and extracted with ether three times. The ether extracts were washed with brine, dried over magnesium sulfate and stripped to give 300 mg of 7-cycloprop-1-enyl-heptanoic acid.

EXAMPLE 11

Preparation of 7-Cycloprop-1-enyl-heptanoic Acid Isopropylamine Salt (Compound 8)

A solution of 7-cycloprop-1-enyl-heptanoic acid ethyl ester in 5 ml of ether was treated with 0.1 g of isopropyl amine at room temperature. The solvent was stripped to give 40 mg of 7-cycloprop-1-enyl-heptanoic acid isopropylamine salt.

EXAMPLE 12

Preparation of 7-Cycloprop-1-enyl-heptanoic Acid Ethyl Ester (Compound 9)

A solution of 220 mg (1.3 mmol) of 1-(7-carboxyheptyl)-cyclopropene in ether was cooled to 0° C. Triethylamine (0.20 g, 2 mmol) was added, then 0.12 g (1.3 mmol) of methylchloroformate was added. After 2 hours at 0° C., the reaction mixture was transferred to a separatory funnel. The ether phase was washed with water (2×) and brine, dried over magnesium sulfate, filtered and stripped. The product was dissolved in ethanol, cooled in an ice bath and treated with 1 ml of a 21% sodium ethoxide in ethanol solution. The reaction mixture was stirred ½ hour, then water and ether were added. The ether phase was washed with 1N sodium hydroxide solution, water, and brine, dried over magnesium sulfate, filtered and stripped to give 10 mg of 75% pure 7-cycloprop-1-enyl-heptanoic acid ethyl ester.

EXAMPLE 13

Preparation of 1-(7-Cyanoheptyl)-cyclopropene (Compound 10)

a. 1-(7-Methanesulfonyloxyheptyl)-cyclopropene

A solution of 3.8 mmol of 1-(7-hydroxyheptyl)-cyclopropene in 50 ml of ether was cooled in an ice bath. Triethylamine (1 ml) and 0.48 g of methanesulfonyl chloride (4.2 mmol) were added and the reaction mixture was stirred for 2½ hours at 0° C. The reaction mixture was washed with water and brine, dried over magnesium sulfate, filtered and stripped to give 1-(7-methanesulfonyloxyheptyl)-cyclopropene which was used without further purification.

b. 1-(7-Cyanoheptyl)-cyclopropene

The crude product from the above reaction was dissolved in 5 ml of DMSO, and treated with 0.99 g (15 mmol) of potassium cyanide. After 6.5 hours at room temperature, the reaction was 72% complete. Ether and water were added. The aqueous phase was washed with more ether. The combined organic phases were washed with water (2×) and brine, dried over magnesium sulfate, filtered and stripped. The product was rapidly chromatographed on silica gel to give 190 mg of 1-(7-cyanoheptyl)-cyclopropene as a colorless liquid, >95% purity.

EXAMPLE 14

Preparation of 1-(7-N,N-Diethylaminoheptyl)-cyclopropene (Compound 11)

a. 1,1,2-Tribromo-2-(7- N,N-diethylaminoheptyl)-cyclopropane

A solution of 1.5 g of 1,1,2-Tribromo-2-(7-hydroxyheptyl)cyclopropane (3.8 mmol) in 10 ml of ether was cooled in an ice bath and treated with 0.77 g (6 mmol) of diisopropylethyl amine. Triflic anhydride (1.18 g, 4.2 mmol) was added dropwise, and the reaction was stirred at 0° C. for ½ hour. Excess diethylamine (roughly 4 ml) was added and the reaction was stirred overnight. The reaction mixture was quenched with water and transferred to a separatory funnel. A small amount of 1N NaOH was added. The aqueous phase was separated, the organic phase was washed twice more with water, then extracted three times with 1N HCl. The acidic washes were treated made basic with aqueous sodium hydroxide solution and extracted three times with ether. The ether was washed with brine, dried over potassium carbonate and stripped. The product was chromatographed through Florisil to give 1,1,2-tribromo-2-(7-N,N-diethylaminoheptyl)-cyclopropane.

b. 1-(7-N,N-Diethylaminoheptyl)-cyclopropene

To a solution of 1.0 g (2.4 mmol) of 1,1,2-tribromo-2-(7-N,N-diethylaminoheptyl)-cyclopropane in 25 ml of THF at −78° C. was added 4.55 ml (1.6 M, 7.3 mmol) of n-BuLi. The reaction mixture was stirred ½ hour, then quenched with methanol. The reaction mixture was warmed to room temperature. Ether was added, the organic phase was washed with water (3×) and brine, dried over magnesium sulfate, and filtered. The solution was stripped on a rotary evaporator with no heat added. A few pipetfuls of toluene were added, and the sample was stripped again to give 1-(7-N,N-diethylaminoheptyl)-cyclopropene.

EXAMPLE 15

Preparation of 1-(7-N,N,-Diethylammoniumheptyl)-cyclopropene Acetate (Compound 12)

A solution of 1-(7-N,N,-diethylamminoheptyl)-cyclopropene in ether was treated with acetic acid. The solvent was removed to give the salt.

EXAMPLE 16

Preparation of 1-(7-N,N,N-Diethylmethylammoniumheptyl)-cyclopropene Iodide (Compound 13)

A mixture of roughly 1.6 mmol of 1-(7-N,N-diethylaminoheptyl)-cyclopropene and excess iodomethane (roughly ½ ml in 5 ml of acetonitrile were stirred at room temperature for two hours. The reaction mixture was stripped to give 300 mg of 1-(7-N,N,N-diethylmethylammoniumheptyl)-cyclopropene iodide.

EXAMPLE 17

Preparation of 1-Hexyloxymethyl-cyclopropene (Compound 14)

a. Preparation of 2-Bromo-3-hexyloxypropene

To a three neck round bottom flask equipped with an addition funnel and an overhead stirrer was added 35 ml of hexane, 42 g of 50% sodium hydroxide and 0.50 g of tetra-n-butylammonium bromide. A mixture of 6.74 g of hexanol (66 mmol) and 20 g (100 mmol) of 2,3-dibromopropene were fed to the well-stirred reaction mixture over a 20 minute period. The reaction was stirred an additional 1 hour, then water was added, and the phases were separated. The organic phase was washed with water and brine, dried over magnesium sulfate, filtered and stripped. The product was fractionally distilled under reduced pressure to give 6.1 g of 95% pure 2-bromo-3-hexyloxypropene.

b. 1,1,2-Tribromo-2-(hexyloxymethyl)cyclopropane

A mixture of 5.9 g of 2-bromo-3-hexyloxypropene(26.7 mmol), 2.05 g of N,N'-dibenzyl-ethane-1,2-bis-(diethylammonium bromide), 10.5 g of 45% potassium hydroxide (84 mmol), 23.3 g of bromoform (92 mmol) and 70 g of methylene chloride were rapidly stirred at room temperature for two days. When the reaction stalled, the reaction mixture was transferred to a separatory funnel and washed with water. The methylene chloride phase was transferred to a flask and treated with the same amount of the phase transfer catalyst and 45% potassium hydroxide, then stirred at room temperature for an additional 3 days. The workup-recharge sequence was repeated once more, and the reaction was stirred one more day at room temperature. The reaction mixture was washed with water, the methylene chloride phase was dried with magnesium sulfate, and then stripped. The product was chromatographed on silica gel with 20% ethyl acetate 80% hexane to give 1.35 g of 87% pure 1,1,2-tribromo-2-(hexyloxymethyl)cyclopropane.

c. 1-Hexyloxymethyl-cyclopropene

A solution of 1.15 g of 1,1,2-tribromo-2-(hexyloxymethyl)cyclopropane (2.9 mmol) in 6 ml of ether was treated at −78° C. with 1.4 ml of methyllithium (1.4 M, 8.8 mmol). After 5 minutes, the reaction mixture was warmed to 0° C. and held at this temperature. The reaction was quenched with saturated ammonium chloride. The reaction mixture was washed with water and brine, dried over magnesium sulfate, filtered and stripped to give 320 mg of 1-hexyloxymethyl-cyclopropene, as a dark yellow liquid.

EXAMPLE 18

Preparation of 1-Pentyloxyethyl-cyclopropene (Compound 15)

a. Preparation of 2-Bromo-4-pentyloxybutene

To a three neck round bottom flask equipped with an addition funnel and an overhead stirrer was added 35 ml of hexane, 42 g of 50% sodium hydroxide and 0.50 g of tetra-n-butylammonium bromide. A mixture of 10 g of 2-bromobuten-4-ol (66 mmol) and 15 g (100 mmol) of 2,3-dibromopropene were fed to the well-stirred reaction mixture. When the addition was complete, the reaction mixture was warmed to for 1 hour, then water was added, and the phases were separated. The organic phase was washed with water and brine, dried over magnesium sulfate, filtered and stripped. A column was run (silica gel, 20% ethyl acetate/80% hexane) to give product that was 70% pure. The more volatile material was removed by distillation under reduced pressure; the material left in the pot was 1.63 g of 99% pure 2-bromo-4-pentyloxybutene.

This olefin was converted to 1-pentyloxyethyl-cyclopropene in the same manner that 2-bromo-3-hexyloxypropene was converted to 1-hexyloxymethyl-cyclopropene.

EXAMPLE 19

Preparation of 3,3-Dipentyl-cyclopropene (Compound 16)

a. 2-Pentyl-hept-1-ene

To a 500 ml, 3 necked, round bottom flask, which was previously placed under a nitrogen atmosphere via use of a Firestone valve, was added 8.50 g (0.0759 mol) of potassium t-butoxide and 27.2 g (0.0762 mol) of methyl triphenylphosphonium bromide and 200 ml tetrahydrofuran. After stirring at room temperature for 4 hours, 12.0 ml (0.0849 mol) of 6-undecanone was added. After 3 days, the reaction mixture was poured onto 200 ml 10% w/v aqueous ammonium chloride. The resulting mixture was transferred to a separatory funnel, extracted twice with hexanes and the phases were separated. The combined organic layers were dried over $MgSO_4$ and filtered. The solvent was removed from the filtrate in vacuo to yield 18.5 g orange solid. This was slurried in 125 ml diethyl ether and gravity filtered through qualitative fluted filter paper rinsing with an additional 125 ml diethyl ether. The solvent was removed from the filtrate in vacuo to yield 12.7 g orange oil. This residue was purified by column chromatography with hexanes to give 6.79 g (47.5% of theoretical) of 2-pentyl-hept-1-ene as an oil.

b. 2,2-Dibromo-1,1-dipentyl-cyclopropane

To a solution of 4.16 g (0.0247 mol) of 2-pentyl-hept-1-ene in 31 ml of pentanes, was added 4.95 g (0.0441 mol) of potassium t-butoxide. While cooling the resulting mixture to an internal temperature of 5° C., 4.01 ml ( 0.0459 mol) of bromoform was added slowly via addition funnel. The reaction mixture was allowed to warm naturally to room temperature and left overnight. To the reaction mixture was added 25 ml of water then 36 ml of 1 N hydrochloric acid. The resulting mixture was transferred to a separatory funnel and the phases were separated. The organic layer was dried over $MgSO_4$ and filtered. The solvent was removed from the filtrate in vacuo to yield 7.00 g (83.4% of theory) of 2,2-dibromo-1,1-dipentyl-cyclopropane as an oil.

c. 2-Bromo-1, 1-dipentyl-cyclopropane

To a solution of 4.00 g (0.0118 mol) of 2,2-dibromo-1, 1-dipentyl-cyclopropane in 11 ml of methanol was added 0.744 ml ( 0.0129 mol) of glacial acetic acid and 0.766 g (0.0118 mol) of zinc dust. After 2 hours 0.744 ml of glacial acetic acid and 0.766 g of zinc dust were added to the mixture. After 2 further hours, the solvent was removed from the reaction mixture in vacuo. The resulting residue was extracted with hexanes and then diethyl ether from water. The combined organic layers were dried over $MgSO_4$ and filtered. The solvent was removed from the filtrate in vacuo to yield 2.1 g (68.2% of theory) of an equal mixture of 2-bromo-1,1-dipentyl-cyclopropane and 1,1-dipentyl-cyclopropane as an oil.

d. 3,3-Dipentyl-cyclopropene

To a solution of 1.90 g of an equal mixture of 2-bromo-1,1-dipentyl-cyclopropane and 1,1-dipentyl-cyclopropane in 10 ml dimethylsulfoxide was added 0.818 g (0.00308 mol) of potassium t-butoxide. The resulting mixture was heated to 85° C. for 5 hours and then stirred at room temperature for 16 hours. To this was added 0.100 g of potassium t-butoxide. The resulting mixture was heated to 85° C. for 2 hours then cooled to room temperature. The reaction mixture was poured onto water and then extracted with diethyl ether. The resulting mixture was transferred to a separatory funnel and the phases were separated. The organic layer was dried over $MgSO_4$ and filtered. The solvent was removed from the filtrate in vacuo to yield 1.90 g of 3,3-dipentyl-cyclopropene mixed in equal parts with 1,1-dipentyl-cyclopropane as an oil.

EXAMPLE 20

Preparation of 1-Pent-2-enyl-2-pentyl-cyclopropene (Compound 17)

A solution of 1.00 g (0.00287 mol) of 1,1,2-tribromo-2-pentyl-cyclopropane in 4 ml of tetrahydrofuran was placed under an inert atmosphere of nitrogen via a Firestone valve. To this mixture, cooling in an ice water bath, was added via syringe 3.58 ml (0.00861 mol) of 1.6M n-butyllithium in hexanes. After 30 minutes, 0.432 ml (0.00287 mol) of tetramethylethylene diamine and 0.339 ml (0.00287 mol) of 1-bromo-2-pentene were added by syringe. The reaction stirred for one hour while warming to room temperature, then for three hours at room temperature. To the resulting mixture was added 2 ml of water. This residue was extracted with diethyl ether. The resulting mixture was transferred to a separatory funnel and the phases were separated. The organic layer was dried over $MgSO_4$ and filtered. The solvent was removed from the filtrate in vacuo to yield 0.200 g (39.1% of theory) of 1-pent-2-enyl-2-pentyl-cyclopropene as an oil.

EXAMPLE 21

Preparation of 1-Pent-2-enyl-3,3-dipentyl-cyclopropene (Compound 18)

A solution of 0.450 g of a 1:1 mixture of 3,3-dipentyl-cyclopropene and 1,1-dipentyl-cyclopropane in 2 ml of tetrahydrofuran with 0.070 (0.000500 mol) ml of diisopropylamine was placed under an inert atmosphere of nitrogen via a Firestone valve. To this mixture, cooling in an ice water bath, was added via syringe 1.72 ml (0.00275 mol) of 1.6M N-butyllithium in hexanes. After 1 hour, 0.478 ml hexamethylphosphoramide and 0.325 ml of 1-bromo-2-pentene were added separately via syringe. The reaction mixture was allowed to warm to room temperature and stirred for 2 days. The reaction was quenched by the addition of 2 ml of water by syringe. This residue was extracted with diethyl ether. The resulting mixture was transferred to a separatory funnel and the phases were separated. The organic layer was dried over $MgSO_4$ and filtered. The solvent was removed from the filtrate in vacuo to yield 0.280 g of 1:1 mixture of 1-pent-2-enyl-3,3-dipentyl-cyclopropene and 1,1-dipentyl-cyclopropane as an oil.

EXAMPLE 22

Preparation of 1-(Oct-7-enyl)-cyclopropene (Compound 19)

Cyclopropene was prepared according to the following reference: Binger, P.; Wedemann, P.; Goddard, R.; Brinker, U.; *J. Org. Chem.*, 1996, 61, 6462.

8-Iodooct-1-ene was prepared by refluxing 5 g of 8-bromooct-1-ene (26 mmol) and 10 g of sodium iodide in 50 ml of acetone for 1 hour. The acetone was stripped and the residue was partitioned between water and ether. The aqueous phase was washed with brine, dried over magnesium sulfate and stripped to give 5.66 g of 8-iodooct-1-ene.

A mixture of 0.43 g (11 mmol) of sodium amide in roughly 15 ml of ammonia was cooled to −78° C. A chilled solution of cyclopropene in ammonia (1:1, 0.85 g, 10 mmol) was poured into the reaction mixture. The reaction mixture was stirred at −78° C. for ½ hour, warmed briefly to the ammonia boiling point, then recooled to −78° C. 8-Iodooct-1-ene (1.2 g, 5 mmol) was added by syringe, and the reaction mixture was warmed to reflux for ½ hour. A few ml of ethanol were added. Ether (25 ml) was slowly added while the ammonia was allowed to distill out of the reaction mixture. The reaction mixture was washed with water, 0.5M HCl (2×), water and brine. It was dried over $MgSO_4$, filtered and stripped. The product was purified by chromatography on silica gel using hexane as the eluent. A 10 mg sample of 67% pure 1-(oct-7-enyl)-cyclopropene was obtained.

EXAMPLE 23

Preparation of 4-(1-Cyclopropenyl)-2-methylbutan-2-ol (Compound 20)

a. 4-Bromo-pent-4-enoic acid ethyl ester

This ester was prepared by the method of Mori, *JOC*, 1983 48, 4062 b. 3-(1,2,2-Tribromo-cyclopropyl)-propionic acid ethyl ester

To a solution made of 12.12 g (58 mmol) of 4-bromo-pent4-enoic acid ethyl ester and 51 g (202 mmol) of bromoform and 100 g of methylene chloride was added 2.0 g of N,N'-dibenzyl-N,N,N',N'-tetramethylethylenediammonium dibromide and 27.1 g (218 mmol) of 45% aqueous potassium hydroxide. The reaction mixture was stirred rapidly for 4 days. The resulting mixture was transferred to a separatory funnel and the phases were separated. The solvent was removed from the isolated organic layer in vacuo. This residue was extracted with hexanes from water. The resulting mixture was transferred to a separatory funnel and the phases were separated. The organic layer was dried over $MgSO_4$ and filtered. The solvent was removed from the filtrate in vacuo. This residue was purified by column chromatography with 10% diethyl ether/hexanes to yield 14.6 g (66.3% of theory) of 3-(1,2,2-tribromo-cyclopropyl)-propionic acid ethyl ester.

c. 4-(1-Cyclopropenyl)-2-methylbutan-2-ol

A solution of 1.08 g (0.00285 mol) of 3-(1,2,2-tribromo-cyclopropyl)-propionic acid ethyl ester in 4 ml of diethyl ether was placed under a nitrogen atmosphere by use of a Firestone valve. While cooling in an ice water bath, 10.2 ml (0.0142 mol) of 1.4 M methyl lithium in diethyl ether was added slowly via syringe. After 15 minutes, 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield 0.380 g of 75% pure with remainder being diethyl ether (79% of theoretical yield corrected for ether) of 4-cycloprop-1-enyl-2-methyl-butan-2-ol as an oil. Product is stored at −80° C.

EXAMPLE 24

Preparation of Methyl Sterculate (Compound 21)

Methyl sterculate (40% purity) was formed by the procedure of Gensler et. al. (Gensler, W. J.; Floyd, M. B.; Yanase, R.; Pober, K. W. *J. Am. Chem. Soc.*, 1970, 92, 2472).

EXAMPLE 25

Preparation of Hex-5-yne 2-octylcycloprop-2-ene-1-carboxylate (Compound 22)

a. Ethyl 2-octylcycloprop-2-ene-1-carboxylate

Ethyl 2-octylcycloprop-2-ene-1-carboxylate was prepared from 1-decyne and ethyl diazoacetate by the method of Mueller, P.; Pautex, N.; *Helv. Chim Acta* 1990, 73,1233.

b. 2-Octylcycloprop-2-ene-1-carboxylic acid

Ethyl 2-octylcycloprop-2-ene-1-carboxylate (1.12 g, 5 mmol) and 100 ml of 0.2 N potassium hydroxide were stirred at room temperature for one week. Ether was added and the phases were separated. The aqueous phase was acidified and extracted with methylene chloride. The organic phase was dried over magnesium sulfate and stripped to give 0.8 g of 2-octylcycloprop-2-ene-1-carboxylic acid.

c. 2-Octylcycloprop-2-ene-1-carbonyl chloride

A solution of 2-octylcycloprop-2-ene-1-carboxylic acid (350 mg, 1.8 mmol) in ether was treated with 0.45 g (3.5 mmol) of oxalyl chloride at room temperature. The reaction mixture was stirred for one hour then stripped to give 330 mg of 2-octylcycloprop-2-ene-1-carbonyl chloride.

d. Hex-5-yne 2-octylcycloprop-2-ene-1-carboxylate

To a solution of 2-octylcycloprop-2-ene-1-carbonyl chloride (330 mg, 1.5 mmol) in 5 ml of ether is added 1.5 ml of triethylamine. 5-Hexyn-1-ol (0.18 g, 1.8 mmol) was added to the reaction mixture, which was stirred at room temperature over the weekend. Water and additional ether were added, and the resulting mixture was transferred to a separatory funnel and the phases were separated. The organic layer was washed with water and brine, dried over $MgSO_4$, filtered and stripped. The product was chromatographed on silica gel to give 40 mg of 60% pure hex-5-yne 2-octylcycloprop-2-ene-1-carboxylate containing roughly 40% 2-octylcycloprop-2-ene-1-carboxylic acid.

EXAMPLE 26

Preparation of 7-Cycloprop-1-enyl-heptanoic Acid (Compound 7) and 8-Cycloprop-1-enyl-octan-2-one (Compound 46)

a. 7-(1,1,2-Tribromo-cyclopropyl)-heptanoic acid 1,1,2-Tribromo-2-(7-hydroxyheptyl)cyclopropane (0.90 g, 2.3 mmol) was dissolved in 60 ml of glacial acetic acid. A solution of 1.0 g (10 mmol) of chromium trioxide dissolved in 14 ml of 90% aqueous acetic acid was added and the reaction mixture was stirred at room temperature for 24 hours. Water (300 ml) was added. The solution was extracted with ether. The ether phase was extracted three times with 1N NaOH solution. A little sodium bisulfite was added. The aqueous extracts were acidified with 6N HCl, and extracted with ether twice. The ether extracts were washed with brine, dried over magnesium sulfate and stripped to give 0.56 g 7-(1,1,2-tribromo-cyclopropyl)-heptanoic acid.

b. 7-Cycloprop-1-enyl-heptanoic acid and 8-Cycloprop-1-enyl-octan-2-one 1,1,2-Tribromo-2-(7-carboxyheptyl)-cyclopropane (1.28 g, 3.1 mmol) was dissolved in 60 ml of ether and cooled to −78° C. Methyllithium (9.0 ml, 12.6 mmol) was added and the reaction was stirred at −78° C. for two hours. The reaction mixture was put in an ice bath for 5 minutes, then recooled to −78° C. until workup. Water was added to the reaction mixture, which was warmed to room temperature. The aqueous phase was separated, and the ether phase was extracted with three times with 1N NaOH solution. The ether phase contained 8-cycloprop-1-enyl-octan-2-one and the combined aqueous extracts contained 7-cycloprop-1-enyl-heptanoic acid.

The ether phase from above was washed with brine, dried over magnesium sulfate and stripped to give 200 mg of 8-cycloprop-1-enyl-octan-2-one, Compound 46.

The combined aqueous extracts containing 7-cycloprop-1-enyl-heptanoic acid were acidified with aqueous HCl, and extracted with ether three times. The ether extracts were washed with brine, dried over magnesium sulfate and stripped to give 300 mg of 7-cycloprop-1-enyl-heptanoic acid, Compound 7.

EXAMPLE 27

Preparation of 8-Cycloprop-1-enyl-octan-2-one O-methyl Oxime (Compound 47)

To a solution of 0.15 g (0.9 mmol) of 8-cycloprop-1-enyl-octan-2-one in 10 mL of methanol cooled in an ice bath was added 0.30 g (3 mmol1) of triethylamine and 0.83 g of a 30–35% aqueous solution of methoxylamine hydrochloride (3 mmol). The ice bath was removed, and the reaction mixture was stirred at room temperature for 1.5 hours. Water and ether were added. The phases were separated and the aqueous phase was washed with ether. The combined ether phases were washed with dilute aqueous hydrochloride acid, water (2x), and brine, then dried over magnesium sulfate, filtered and stripped. Column chromatography gave 50 mg of 8-cycloprop-1-enyl-octan-2-one O-methyl oxime (Compound 47) as a 30% solution in ether. The ratio of oxime isomers was 3:1.

EXAMPLE 28

Preparation of 7-Cycloprop-1-enyl-heptanoic Acid Diethylamide (Compound 48)

A solution of 7-cycloprop-1-enyl-heptanoic acid (0.25 g, 1.5 mmol) in 10 ml of ether was cooled in an ice bath and treated with 0.3 mL of triethyl amine. Methyl chloroformate (0.16 g, 17 mmol) was added, and the reaction was stirred for 1.5 hours. Excess diethylamine was added while the reaction was still cooled in an ice bath, and the reaction was stirred for one half hour. Additional ether and water were added, and the aqueous phase was acidified to pH 1 with aqueous HCl. The phases were separated, and the organic phase was washed with water, 1N sodium hydroxide, water and brine. The organic phase was dried over magnesium sulfate, filtered and stripped. Column chromatography gave 70 mg of colorless liquid 7-cycloprop-1-enyl-heptanoic acid diethylamide (Compound 48) in 74% purity.

EXAMPLE 29

In a manner similar to those described above, the following compounds were made:

TABLE 3

Additional compounds

| Compound | $R_1$ | $R_2$ | $R_3$ | $R_4$ | Comments |
|---|---|---|---|---|---|
| 23 | Octyl | H | H | H | |
| 24 | n-Nonyl | H | H | H | 1:1 mixture with 1-bromo-2-nonylcyclopropene |
| 25 | n-Decyl | H | H | H | |
| 26 | n-Heptyl | H | H | H | |
| 27 | Undecyl | H | H | H | 70% purity |
| 28 | 3-Ethylheptyl | H | H | H | |
| 29 | Tridecyl | H | H | H | |
| 30 | 2-(2-methoxy-ethoxy)-ethoxymethyl | H | H | H | |
| 31 | n-Amyl | H | H | H | |
| 32 | 2-Methylheptyl | H | H | H | |
| 33 | 2-propionyl-oxyethane | H | H | H | 75% purity |
| 34 | 6-Methylheptyl | H | H | H | |
| 35 | 3,5,5-Tri-methylhexyl | H | H | H | |
| 36 | 7-Octenyl | H | H | H | |
| 37 | 5,5,5-Tri-fluoropentyl | H | H | H | Tested as a 51% solution in ether |
| 38 | Pentadecyl | H | H | H | |
| 39 | 4,8-Nonyl | H | H | H | |
| 40 | Dodecyl | H | H | H | |
| 41 | Di-n-butyl-aminomethyl | H | H | H | 1:4 mixture with 2-bromo-3-(di-N-butylamino)prop-1-ene |

TABLE 3-continued

Additional compounds

| Compound | $R_1$ | $R_2$ | $R_3$ | $R_4$ | Comments |
|---|---|---|---|---|---|
| 42 | Tetradecyl | H | H | H | |
| 43 | 3,3-Dimethyl-butyl | H | H | H | |
| 44 | Hexyl | H | Hexyl | H | 70% purity |
| 45 | Pentyl | Pentyl | H | H | |

EXAMPLE 30

The compounds described above were characterized using a variety of spectroscopic techniques. The NMR data for compounds 1–45 is given in Table 4. For compounds containing impurities, the chemical shifts of the impurities are not reported, and the integrals are adjusted to reflect only the contribution of the target compound.

TABLE 4

NMR Data

| Compound | NMR data |
|---|---|
| 1 | (CDCl3) 0.9(m, 5H), 1.3(m, 6H), 1.5(m, 2H), 2.5(t, 2H), 6.4(t, 1H). |
| 2 | (CDCl3): 0.88(t, 3H), 1.15–1.35(m, 14H), 1.5(m, 1H), 7.3(s, 2H). |
| 3 | (CDCl3): 0.88(d, 2H), 1.2–1.45(m, 6H), 1.5–1.7(m, 4H), 2.45(dt, 2H), 3.33(s, 3H), 3.37(t, 2H), 6.45(t, 1H). |
| 4 | (CDCl3): 0.89(t and d, 5H), 1.2–1.45(m, 4H), 1.45–1.6(m, 4H), 1.6–1.75(m, 2H), 2.05–2.2(m, 4H), 2.48(dt, 2H), 6.45(s, 1H). |
| 5 | (CDCl3): 0.88(d, 2H), 1.2–1.45(m, 6H), 1.5–1.7(m, 4H), 1.8(bs, 1H), 2.47(dt, 2H), 3.63(t, 2H), 6.4(s, 1H). |
| 6 | (CDCl3): 0.88(d, 2H), 1.25–1.45(m, 6H), 1.5–1.75 (m, 4H), 2.05(s, 3H), 2.5(dt, 2H), 4.05 (t, 2H), 6.45(s, 1H). |
| 7 | (CDCl3): 0.88(d, 2H), 1.25–1.45(m, 4H), 1.5–1.8(m, 4H), 2.36(t, 2H), 2.48(dt, 2H), 6.44(t, 1H). |
| 8 | (CDCl3): 0.88(d, 2H), 1.22(d, 6H), 1.3–1.45(m, 4H), 1.5–1.7(m, 4H), 2.24(t, 2H), 2.47(dt, 2H), 3.2(m, 1H), 3.4–3.9(bs, 2H and water), 6.45(t, 1H). |
| 9 | (CDCl3): 0.88(d, 2H), 1.2(t, 3H), 1.25–1.45(m, 4H), 1.5–1.8(m, 4H), 2.28(t, 2H), 2.45(dt, 2H), 4.13(q, 2H), 6.45(s, 1H). |
| 10 | (CDCl3): 0.88(d, 2H), 1.4–1.55(m, 6H), 1.55–1.75(m, 4H), 2.34(t, 2H), 2.48(dt, 2H), 6.44(t, 1H). |
| 11 | (CDCl3): 0.88(d, 2H), 1.04(t, 6H), 1.2–1.4(m, 6H), 1.4–1.55(m, 2H), 1.55–1.65(m, 2H), 2.4–2.5(m, 4H), 2.55(q, 4H), 6.44(s, 1H). |
| 12 | (CDCl3): 0.88(d, 2H), 1.25(t, 6H), 1.3–1.4(m, 6H), 1.5–1.7(m, 4H), 2.02(s, 3H), 2.45(t, 2H), 2.85–2.95(m, 2H), 3.05(q, 4H), 6.45(s, 1H). |
| 13 | (CDCl3): 0.88(d, 2H), 1.3–1.45(t and m, 12H), 1.6(quintet, 2H), 1.75(m, 2H), 2.45(dt, 2H), 3.27(s, 3H), 3.35–3.5(m, 2H), 3.61(q, 4H), 6.45(s, 1H). |
| 14 | (CDCl3): 0.89(t, 3H), 1.06(d, 2H), 1.2–1.45(m, 6H), 1.5–1.7(m, 4H), 3.5(t, 2H), 4.51(d, 2H), 6.74(t, 1H). |
| 15 | (CDCl3): 0.90(m, 5H), 1.2–1.45(m, 4H), 1.5–1.7(m, 2H), 2.76 (dt, 2H), 3.45(t, 2H), 3.65(t, 2H), 6.55(t, 1H). |
| 16 | (Acetone-d6): 0.7(m, 6H), 1.05–1.3(m, 12H), 1.85(m, 4H), 7.25(s, 2H). |
| 17 | (CDCl3): 0.85–1.05(m, 8H), 1.15–1.35(m, 4H), 1.45–1.65(m, 2H), 2–2.1(m, 2H), 2.4(m, 2H), 3.15(m, 2H), 5.4–5.6(m, 2H). |
| 18 | (Acetone-d6): 0.9(m, 6H), 1.0(m, 3H), 1.05–1.55(m, 18H), 2.86(d, 2H), 5.4–5.75(m, 2H), 6.85(s, 1H). |
| 19 | (CDCl3): 0.88 (d, 2H), 1.25–1.5(m, 6H), 1.5–1.7(m, 2H), 1.95–2.15(m, 2H), 2.47(dt, 2H), 4.92(dd, 1H), 4.98(dd, 1H), 5.8(m, 1H), 6.44(t, 1H). |
| 20 | (CDCl3): 0.9(d, 2H), 1.25(s, 6H), 1.35(m, 2H), 1.65(s, 1H), 1.8(t, 2H), 6.45(t, 1H). |

TABLE 4-continued

NMR Data

| Compound | NMR data |
|---|---|
| 21 | (CDCl3): 0.76(s, 2H), 0.88(t, 3H), 1.15–1.4(m, 18H), 1.45–1.7(m, 4H), 2.1(m, 2H), 2.3(t, 2H), 2.4(t, 3H), 3.67(s, 3H) |
| 22 | (CDCl3): 0.88(t, 3H), 1.2–1.45(m, 10H), 1.5–1.7(m, 4H), 1.75(m, 2H), 1.95 (t, 1H), 2.18(s, 1H), 2.23(dt, 2H), 2.4–2.55(m, 2H), 4.05–4.15(m, 2H), 6.32(s, 1H). |
| 23 | (CDCl3): 0.9(t and s, 5H), 1.2–1.5(m, 10H), 1.6(m, 2H), 2.5(t, 2H), 6.42(s, 1H). |
| 24 | (CDCl3): 0.9(t and s, 5H), 1.2–1.5(m, 12H), 1.7(m, 2H), 2.4(t, 2H), 6.45(s, 1H). |
| 25 | (CDCl3): 0.88(t and s, 5H), 1.2–1.5(m, 14H), 1.7(m, 2H), 2.5(t, 2H), 6.45(s, 1H). |
| 26 | (CDCl3): 0.88(t and d, 5H), 1.2–1.5(m, 8H), 1.7(m, 2H), 2.5(t, 2H), 6.42(s, 1H). |
| 27 | (CDCl3): 0.88(t and d, 5H), 1.2–1.5(m, 16H), 1.7(m, 2H), 2.4(t, 2H), 6.4(s, 1H). |
| 28 | (CDCl3): 0.8(m, 8H), 1.1–1.4(m, 10H), 1.7(m, 2H), 2.4(t, 2H), 6.42(s, 1H). |
| 29 | (CDCl3): 0.9(m, 5H), 1.2–1.5(m, 20H), 1.6(m, 2H), 2.4(t, 2H), 6.4(s, 1H). |
| 30 | (CDCl3): 1.06(d, 2H), 3.39(s, 3H), 3.5–3.8(m, 8H), 4.59(d, 2H), 6.75(t, 1H). |
| 31 | (CDCl3): 0.9(m, 5H), 1.3(m, 4H), 1.6(m, 2H), 2.5(t, 2H), 6.4(s, 1H). |
| 32 | (CDCl3): 0.85–0.95(m, 8H), 1.1–1.4(m, 8H), 1.8(m, 1H), 2.25–2.6(2dd, 2H), 6.45(s, 1H). |
| 33 | (CDCl3): 0.93(d, 2H), 1.12(t, 3H), 2.32(q, 2H), 2.82(dt, 2H), 4.32(t, 2H), 6.60(s, 1H). |
| 34 | (CDCl3): 0.88(m, 8H), 1.1–1.4(m, 5H), 1.45–1.17(m, 4H), 2.45(t, 2H), 6.45(s, 1H). |
| 35 | (CDCl3): 0.88(m, 14H), 1–1.6(m, 7H), 2.4(t, 2H), 6.45(s, 1H). |
| 36 | (CDCl3): 0.9(m, 8H), 1–1.8(m, 7H), 2.5(m, 2H), 6.4(t, 1H). |
| 37 | (CDCl3): 0.90(d, 2H), 1.5–1.75(m, 4H), 2.0–2.2 (m, 2H), 2.55(dt, 2H), 4.92(dd, 1H), 4.98(dd, 1H), 5.8(m, 1H), 6.5(t, 1H). |
| 38 | (CDCl3): 0.88(m, 5H), 1.15–1.3(m, 24H), 1.55(m, 2H), 2.45(t, 2H), 6.45(s, 1H). |
| 39 | (CDCl3): 0.9(d, 11H), 1.05–1.7(m, 12H), 2.45(t, 2H), 6.45(s, 1H). |
| 40 | (CDCl3): 0.88(m, 5H), 1.15–1.45(m, 16H), 1.6(m, 4H), 2.45(t, 2H), 6.45(s, 1H). |
| 41 | (CDCl3): 0.88(d, 2H), 1.05(t, 6H), 1.3–1.55(m, 8H), 2.4–2.65(m, 4H), 3.65(s, 2H), 6.6(t, 1H). |
| 42 | (CDCl3): 0.88(m, 5H), 1.25(s, 24H), 2.45(t, 2H), 6.45(s, 1H). |
| 43 | (CDCl3): 0.9(m, 11H), 1.45–1.55(m, 2H), 2.4–2.55(m, 2H), 6.4(s, 1H). |
| 44 | (CDCl3): 0.9(m, 6H), 1.25–1.45(m, 17H), 1.5(m, 2H), 2.45(t, 2H), 6.65(s, 1H). |
| 45 | (CDCl3): 0.77(s, 2H), 0.9(t, 6H), 1.3(m, 4H), 1.5(m, 8H), 2.4(m, 4H). |
| 46 | (CDCl3): 0.88(d, 2H), 1.2–1.4(m, 4H), 1.5–1.7(m, 4H), 2.14(s, 3H), 2.43(t, 2H), 2.47(dt, 2H), 6.45(t, 1H). |
| 47 | (CDCl3): 0.88(d, 2H), 1.2–1.45(m, 4H), 1.5–1.7(m, 4H), 1.82(major isomer), 1.85(minor isomer) (2s, 3H), 2.15(major isomer) 2.30(minor isomer) (2t, 2H), 2.47(dt, 2H), 3.80(minor isomer), 3.83(major isomer) (2s, 3H), 6.45(t, 1H). |
| 48 | (CDCl3): 0.87(d, 2H), 1.1, 1.15(2tx, 6H), 1.3–1.45(m, 4H), 1.5–1.75(m, 4H), 2.29(t, 2H), 2.47(dt, 2H), 3.30(q, 2H), 3.37(q, 2H), 6.43(t, 1H). |

EXAMPLE 31

Biological Activity

Tomato Epinasty Test Protocols

The test procedure is designed to determine the ability of an compound according to the present invention to block the epinastic growth response induced by ethylene in tomato plants when the compound is administered either as a volatile gas or as a component of a spray solution.

Treatment chambers are of an appropriate size for the test plants and are airtight. Each is fitted with a reusable septum to be used for injection of ethylene.

Test plants are Patio variety tomato seedlings planted two plants per three inch square plastic pot.

Volatile gas treatment entails placing two pots of Patio var. tomatoes into a polystyrene 4.8 L volume treatment chamber along with one-half (upper or lower section) of a 50×9 mm plastic Petri dish containing a Gelman filter pad. The appropriate amount of experimental compound, dissolved in 1.0 ml acetone, is pipetted onto the filter pad and the chamber immediately sealed. Four hours later ethylene gas equal to 10 ppm v/v final concentration is injected into the sealed chamber. Sixteen hours later the chambers are opened in an exhaust hood, allowed to air and the plants scored visually for the degree of protection against ethylene-induced epinasty conferred by the experimental compound when compared to ethylene treated and untreated controls on a scale of 0 to 10. A rating of 10 means complete protection. A rating of 0 means no protection from the effects of ethylene.

Spray application treatment entails using a DeVilbiss atomizer to completely cover all foliage and stems of two pots of Patio var. tomato plants with the appropriate amount of experimental compound dissolved in 10% acetone/90% water with 0.05% Silwett L-77 surfactant. Plants are air-dried in a drying hood for four hours then transferred to a 4.8 L polystyrene chamber which is sealed.

Ethylene gas equal to 10 ppm v/v final concentration is injected into the sealed chamber. Sixteen hours later the chambers are opened in an exhaust hood, allowed to air and the plants scored visually for the degree of protection against ethylene-induced epinasty conferred by the experimental compound when compared to ethylene treated and untreated controls on a scale of 0 to 10. A rating of 10 means complete protection. A rating of 0 means no protection from the effects of ethylene.

When applied as a spray in the tomato epinasty test, 1-pentylcyclobutene was superior to 1-butylcyclobutene. The pentyl analog was rated 10 (complete protection), while the butyl analog was rated 5.

The activity of the compounds of this invention in the tomato epinasty test when applied as a gas is given in the table.

TABLE 5

Activity of compounds according to the present invention in the tomato epinasty test

| Compound | Gas 1000 ppm | Gas 750 ppm | Gas 500 ppm | Gas 10 ppm |
|---|---|---|---|---|
| 1 | | | | 10 |
| 2 | 10 | | | 0 |
| 3 | | | | 9.5 |
| 4 | | | | 10 |
| 5 | 10 | | | 0 |
| 6 | 10 | | | 0 |
| 7 | 8 | | | 3 |
| 8 | | | 8 | 0 |
| 9 | | | | 4 |
| 10 | 10 | | | 2 |
| 11 | 10 | | | 3 |
| 12 | 10 | | | 2 |
| 13 | | | | 6 |

TABLE 5-continued

Activity of compounds according to the present invention in the tomato epinasty test

| Compound | Gas 1000 ppm | Gas 750 ppm | Gas 500 ppm | Gas 10 ppm |
|---|---|---|---|---|
| 14 | | | | 10 |
| 15 | | | | 10 |
| 16 | 10 | | | 0 |
| 17 | 10 | | | 0 |
| 18 | 10 | | | 0 |
| 19 | | | | 10 |
| 20 | 8 | | | 0 |
| 21 | 9 | | | 5 |
| 22 | | | 9 | 0 |
| 23 | | | | 10 |
| 24 | | | | 9.5 |
| 25 | | | | 9 |
| 26 | | | | 10 |
| 27 | | | | 10 |
| 28 | | | | 9 |
| 29 | 10 | | | 3.5 |
| 30 | 10 | | | 3 |
| 31 | | | | 10 |
| 32 | | | | 9.5 |
| 33 | 10 | | | 0 |
| 34 | | | | 10 |
| 35 | | | | 10 |
| 36 | | | | 10 |
| 37 | | | | 10 |
| 38 | 10 | | | 4.5 |
| 39 | | | | 10 |
| 40 | 10 | | | 4 |
| 41 | 10 | | | 3 |
| 42 | 10 | | | 2 |
| 43 | | | | 10 |
| 44 | 10 | | | 0 |
| 45 | 10 | | | 0 |
| 46 | 9 | | | 3 |
| 47 | | | | 9.5 |
| 48 | 7 | | | 0 |

The foregoing embodiments and examples are illustrative of the present invention and are not to be construed as limiting thereof. The invention is defined by the following claims, with equivalents of the claims to be included therein.

That which is claimed is:

1. A method of inhibiting an ethylene response in a plant, comprising applying to the plant an effective ethylene response-inhibiting amount of a compound of Formula I:

(I)

wherein:
n is a number from 1 to 4; and
each R is independently a saturated or unsaturated, linear or branched-chain, unsubstituted or substituted, $C_5$–$C_{20}$ alkyl, alkenyl, or alkynyl, wherein at least one R is a saturated or unsaturated, linear or branched-chain, unsubstituted or substituted $C_5$ alkyl, alkenyl, or alkynyl.

2. The method according to claim 1, wherein n is 1 or 2.

3. The method according to claim 1, wherein n is 1.

4. The method according to claim 1, wherein said applying step is carried out by contacting said plant to a composition comprising said compound and an inert carrier.

5. The method according to claim 1, wherein said applying step is carried out by contacting said plant to a gas of said compound.

6. The method according to claim 1, wherein said applying step is carried out by spraying said plant with a solution comprising said compound.

7. The method according to claim 1, wherein said applying step is carried out by contacting said plant to a solid comprising said compound.

8. The method according to claim 1, wherein said ethylene response is fruit ripening.

9. The method according to claim 1, wherein said ethylene response is vegetable ripening.

10. The method according to claim 1, wherein said ethylene response is flower senescence.

11. The method according to claim 1, wherein said ethylene response is abscission.

12. The method according to claim 1, wherein said plant is a harvested fruit.

13. The method according to claim 1, wherein said plant is a harvested vegetable.

14. The method according to claim 1, wherein at least one R is an alkyl, alkenyl, or alkynyl substituted with at least one substituent selected from the group consisting of halogen, amino, alkoxy, carboxy, alkoxycarbonyl, oxycarbonylalkyl and hydroxy.

15. The method according to claim 1, wherein at least one of the carbon atoms in at least one R group is replaced by at least one constituent selected from the group consisting of ester groups, nitrites, amines, amine salts, acids, acid salts, esters of acids, hydroxyl groups, halogen groups, and heteroatoms selected from the group consisting of oxygen and nitrogen.

16. The method according to claim 1, wherein the compound is selected from the group consisting of 3,3-dipentyl-cyclopropene, 1-pent-2-enyl-2-pentyl-cyclopropene, 1-pent-2-enyl-3,3-dipentyl-cyclopropene, 4-(1-cyclopropenyl)-2-methylbutan-2-ol, 1-(n-amyl)-cyclopropene, 1-(5,5,5-trifluoropentyl)-cyclopropene, and 1,2-dipentyl-cyclopropene.

17. A method of prolonging the life of a cut flower, comprising applying to the cut flower an effective life-prolonging amount of a compound of Formula I:

(I)

wherein:
n is a number from 1 to 4; and
each R is independently a saturated or unsaturated, linear or branched-chain, unsubstituted or substituted, $C_5$–$C_{20}$ alkyl, alkenyl, or alkynyl, wherein at least one R is a saturated or unsaturated, linear or branched-chain, unsubstituted or substituted $C_5$ alkyl, alkenyl, or alkynyl.

18. The method according to claim 17, wherein n is 1 or 2.

19. The method according to claim 17, wherein n is 1.

20. The method according to claim 17, wherein said applying step is carried out by contacting said plant to a composition comprising said compound and an inert carrier.

21. The method according to claim 17, wherein said applying step is carried out by contacting said plant to a gas of said compound.

22. The method according to claim 17, wherein said applying step is carried out by spraying said plant with a solution comprising said compound.

23. The method according to claim 17, wherein said applying step is carried out by contacting said plant to a solid comprising said compound.

24. The method according to claim 17, wherein at least one R is an alkyl, alkenyl, or alkynyl substituted with at least one substituent selected from the group consisting of halogen, amino, alkoxy, carboxy, alkoxycarbonyl, oxycarbonylalkyl, and hydroxy.

25. The method according to claim 17, wherein at least one of the carbon atoms in at least one R group is replaced by at least one constituent selected from the group consisting of ester groups, nitriles, amines, amine salts, acids, acid salts, esters of acids, hydroxyl groups, halogen groups, and heteroatoms selected from the group consisting of oxygen and nitrogen.

26. The method according to claim 17, wherein the compound is selected from the group consisting of 3,3-dipentyl-cyclopropene, 1-pent-2-enyl-2-pentyl-cyclopropene, 1-pent-2-enyl-3,3-dipentyl-cyclopropene, 4-(1-cyclopropenyl)-2-methylbutan-2-ol, 1-(n-amyl)-cyclopropene, 1-(5,5,5-trifluoropentyl)-cyclopropene, and 1,2-dipentyl-cyclopropene.

27. A method of inhibiting an ethylene response in a plant, comprising applying to the plant an effective ethylene response-inhibiting amount of a compound of Formula I:

(I)

wherein:
n is a number from 1 to 4;
each R is independently a saturated or unsaturated, linear or branched-chain, unsubstituted or substituted, $C_6$–$C_{20}$ alkyl, alkenyl, or alkynyl; and
wherein said compound is selected from the group consisting of 1-(7-methoxyheptyl)-cyclopropene, 1-(7-hydroxymethyl)-cyclopropene, 1-(7-acetoxyheptyl)-cyclopropene, 7-cycloprop-1-enyl-heptanoic acid, 7-cycloprop-1-enyl-heptanoic acid isopropylamine salt, 7-cycloprop-1-enyl-heptanoic acid ethyl ester, 1-(7-cyanoheptyl)-cyclopropene, 1-(7-N,N-diethylaminoheptyl)-cyclopropene, 1-(7-N,N-diethylammoniumheptyl)-cyclopropene acetate, 1-(7-N,N-diethylmethylammonium-heptyl)-cyclopropene iodide, 1-hexyloxymethyl-cyclopropene, 1-pentyloxyethyl-cyclopropene, methyl sterculate, 1-(n-nonyl)-cyclopropene, 1-(n-decyl)-cyclopropene, 1-(n-heptyl)-cyclopropene, 1-(undecyl)-cyclopropene, 1-(3-ethylheptyl)-cyclopropene, 1-(tridecyl)-cyclopropene, 1-(2-(2-methoxy-ethoxy)-ethoxymethyl)-cyclopropene, 1-(2-methylheptyl)-cyclopropene, 1-(2-propionyloxyethyl)-cyclopropene, 1-(6-methylheptyl)-cyclopropene, 1-(3,5,5 -trimethylhexyl)-cyclopropene, 1-pentadecyl-cyclopropene, 1-(4,8-nonyl)-cyclopropene, 1-dodecyl-cyclopropene, 1-(di-n-butylaminomethyl)-cyclopropene, 1-tetradecyl-cyclopropene, 1-(3,3-dimethylbutyl)-cyclopropene, 1,3-dihexyl-cyclopropene, 8-cycloprop-1-enyl-octan-2-one, 8-cycloprop-1-enyl-octan-2-one O-methyl-oxime, 7-cycloprop-1-enyl-heptanoic acid diethylamide, 1-(oct-7-enyl)-cyclopropene, 1-(7-octenyl)-cyclopropene, 1-(undec-5-ynl)-cyclopropene, and hex-5-yne-2-octylcycloprop-2-ene-1-carboxylate.

28. The method according to claim 27, wherein said applying step is carried out by contacting said plant to a composition comprising said compound and an inert carrier.

29. A method of prolonging the life of a cut flower, comprising applying to the cut flower an effective life-prolonging amount of a compound of Formula I:

(I)

wherein:
n is a number from 1 to 4; and
each R is independently a saturated or unsaturated, linear or branched-chain, unsubstituted or substituted, $C_6$–$C_{20}$ alkyl, alkenyl, or alkynyl; and
wherein said compound is selected from the group consisting of 1-(7-methoxy-heptyl)-cyclopropene, 1-(7-hydroxymethyl)-cyclopropene, 1-(7-acetoxyheptyl)-cyclopropene, 7-cycloprop-1-enyl-heptanoic acid, 7-cycloprop-1-enyl-heptanoic acid isopropylamine salt, 7-cycloprop-1-enyl-heptanoic acid ethyl ester, 1-(7-cyanoheptyl)-cyclopropene, 1-(7-N,N-diethylaminoheptyl)-cyclopropene, 1-(7-N,N-diethylammoniumheptyl)-cyclopropene acetate, 1-(7-N,N-diethylmethylammonium-heptyl)-cyclopropene iodide, 1-hexyloxymethyl-cyclopropene, 1-pentyloxyethyl-cyclopropene, methyl sterculate, 1-(n-nonyl)-cyclopropene, 1-(n-decyl)-cyclopropene, 1-(n-heptyl)-cyclopropene, 1-(undecyl)-cyclopropene, 1-(3-ethylheptyl)-cyclopropene, 1-(tridecyl)-cyclopropene, 1-(2-(2-methoxy-ethoxy)-ethoxymethyl)-cyclopropene, 1-(2-methylheptyl)-cyclopropene, 1-(2-propionyloxy-ethyl)-cyclopropene, 1-(6-methylheptyl)-cyclopropene, 1-(3,5,5-trimethylhexyl)-cyclopropene, 1-pentadecyl-cyclopropene, 1-(4,8-nonyl)-cyclopropene, 1-dodecyl-cyclopropene, 1-(di-n-butylaminomethyl)-cyclopropene, 1-tetradecyl-cyclopropene, 1-(3,3-dimethylbutyl)-cyclopropene, 1,3-dihexyl-cyclopropene, 8-cycloprop-1-enyl-octan-2-one, 8-cycloprop-1-enyl-octan-2-one O-methyl-oxime, 7-cycloprop-1-enyl-heptanoic acid diethylamide, 1-(oct-7-enyl)-cyclopropene, 1-(7-octenyl)-cyclopropene, 1-(undec-5-ynl)-cyclopropene, and hex-5-yne-2-octylcycloprop-2-ene-1-carboxylate.

30. The method according to claim 29, wherein said applying step is carried out by contacting said plant to a composition comprising said compound and an inert carrier.

* * * * *